United States Patent
Stoianovici et al.

(10) Patent No.: US 12,251,141 B2
(45) Date of Patent: Mar. 18, 2025

(54) VERTEBRAL BODY MANIPULATION DEVICE AND METHODS

(71) Applicant: The Johns Hopkins University, Baltimore, MD (US)

(72) Inventors: Dan Stoianovici, Reistertown, MD (US); Jean-Paul Wolinsky, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 130 days.

(21) Appl. No.: 17/843,300

(22) Filed: Jun. 17, 2022

(65) Prior Publication Data

US 2022/0313324 A1 Oct. 6, 2022

Related U.S. Application Data

(63) Continuation of application No. 16/659,060, filed as application No. PCT/US2018/028491 on Apr. 20, 2018, now Pat. No. 11,382,672.

(60) Provisional application No. 62/488,347, filed on Apr. 21, 2017.

(51) Int. Cl.
*A61B 17/70* (2006.01)
*A61B 17/02* (2006.01)

(52) U.S. Cl.
CPC .. *A61B 17/7079* (2013.01); *A61B 2017/0256* (2013.01)

(58) Field of Classification Search
CPC ............ A61B 17/7076; A61B 17/7077; A61B 17/7079; A61B 17/708; A61B 17/7082

USPC ......................................................... 606/105
See application file for complete search history.

(56) References Cited

U.S. PATENT DOCUMENTS

| | | | |
|---|---|---|---|
| 7,776,051 B2 | 8/2010 | Colleran et al. | |
| 8,951,258 B2 | 2/2015 | Peultier et al. | |
| 9,161,782 B2 | 10/2015 | Fanger et al. | |
| 9,161,787 B2* | 10/2015 | Wolinsky | A61B 17/708 |
| 9,211,149 B2 | 12/2015 | Hoefer et al. | |
| 9,561,062 B2 | 2/2017 | Hayes et al. | |
| 11,382,672 B2* | 7/2022 | Stoianovici | A61B 17/7079 |
| 2005/0245928 A1* | 11/2005 | Colleran | A61B 17/708 606/86 A |

(Continued)

OTHER PUBLICATIONS

Heary RF, Madhavan K. The history of spinal deformity. Neurosurgery. 2008, A5-15, 63(3).

(Continued)

*Primary Examiner* — Eduardo C Robert
*Assistant Examiner* — Christina NegrelliRodriguez
(74) *Attorney, Agent, or Firm* — Fox Rothschild LLP

(57) ABSTRACT

Featured is a vertebral body manipulation instrument or vertebral body manipulation device being configured and arranged to allow correction of vertebral translation. Such a vertebral body manipulation device embodies one or more identical modules that are configured as needed for correcting the deformity. Such a vertebral body manipulation device also is usable in combination with a plurality of vertebral anchors, such vertebral anchors being any such vertebral anchors as are known to those skilled in the art (e.g., conventional spinal pedicle screw instrumentation) or hereinafter developed so as to form a spinal implant system. Also featured are treatment methods utilizing such a vertebral body manipulation device.

20 Claims, 11 Drawing Sheets

(56) References Cited

U.S. PATENT DOCUMENTS

| | | |
|---|---|---|
| 2008/0077139 A1 | 3/2008 | Landry et al. |
| 2008/0119862 A1 | 5/2008 | Wicker et al. |
| 2012/0095512 A1 | 4/2012 | Nihalani |

OTHER PUBLICATIONS

Watters III WC, et al. An evidence-based clinical guideline for the diagnosis and treatment of degenerative lumbar spondylolisthesis. The Spine Journal. 2009, 609-14, 9(7).

Barrey C, et al. Sagittal balance of the pelvis-spine complex and lumbar degenerative diseases. A comparative study about 85 cases. European Spine Journal. 2007, 1459-67, 16(9).

El-Rich M, et al. A biomechanical study of L5-S1 low-grade isthmic spondylolisthesis using a personalized finite element model. Studies in health technology and informatics. 2006, 431-4, 123.

Labelle H, et al. The importance of spino-pelvic balance in L5-s1 developmental spondylolisthesis: a review of pertinent radiologic measurements. Spine. 2005, S27-34, 30(6).

Ailon T, et al. Degenerative spinal deformity. Neurosurgery. 2015, S75-91, 77.

Ettinger B, et al., J Bone Miner Res. 1992, 449-456,7(4).

Schwab F, et al. Adult scoliosis: prevalence, SF-36, and nutritional parameters in an elderly volunteer population. Spine, 1976, 1082-1085, 30 (9).

Hresko MT, et al. Classification of high-grade spondylolistheses based on pelvic version and spine balance: possible rationale for reduction. Spine. 2007,2208-13, 32(20).

Kepler CK, et al. Restoration of lordosis and disk height after single-level transforaminal lumbar interbody fusion. Orthopaedic surgery. 2012, 15-20, 4(1).

Slone RM, et al. Spinal fixation. Part 2. Fixation techniques and hardware for the thoracic and lumbosacral spine. Radiographics. 1993, 521-43, 13(3).

Weinstein JN, et al. Surgical versus nonsurgical treatment for lumbar degenerative spondylolisthesis. New England Journal of Medicine. 2007, 2257-70,356(22).

Chrastil J, Patel AA. Complications associated with posterior and transforaminal lumbar interbody fusion. JAAOS—Journal of the American Academy of Orthopaedic Surgeons. 2012, 283-91,20(5).

Kasliwal MK, et al. Does prior short-segment surgery for adult scoliosis impact perioperative complication rates and clinical outcome among patients undergoing scoliosis correction?. Journal of Neurosurgery: Spine. 2012, 128-33, 17(2).

Ogilvie JW. Complications in spondylolisthesis surgery. Spine. 2005, S97-101,30(6S).

Quraishi NA, et al. Access related complications in anterior lumbar surgery performed by spinal surgeons. Eur Spine J. 2013, S16-20, 22 Suppl 1.

Sansur, C. A., et al.(2010). Morbidity and mortality in the surgical treatment of 10,242 adults with spondylolisthesis, Journal of Neurosurgery: Spine SPI,2010, 589-593, 13(5).

Smith JS, et al. Rates and causes of mortality associated with spine surgery based on 108,419 procedures: a review of the Scoliosis Research Society Morbidity and Mortality Database. Spine. 2012, 1975-1982, 37(23).

Smith JS, et al. Short-term morbidity and mortality associated with correction of thoracolumbar fixed sagittal plane deformity: a report from the Scoliosis Research Society Morbidity and Mortality Committee. Spine (Phila Pa 1976). 2011, 958-64, 36(12).

Chen L Chin Med J (Engl). 2003 , 99-103, 116(1).

Kasliwal MK, et al. Short-term complications associated with surgery for high-grade spondylolisthesis in adults and pediatric patients: a report from the scoliosis research society morbidity and mortality database. Neurosurgery. 2012, 109-16,71(1).

Tian NF, Xu HZ. Image-guided pedicle screw insertion accuracy: a meta-analysis. International orthopaedics. 2009, 895-903, 33.

Fu TS, et al. Pedicle screw insertion: computed tomography versus fluoroscopic image guidance. International orthopaedics. 2008, 517-21, 32.

Schlenk RP, et al. Biomechanics of spinal deformity. Neurosurg Focus. 2003, e2, 14(1).

Heary RF, The history of spinal deformity. Neurosurgery. 2008, A5-15, 63(3).

International Search Report and Written Opinion dated Aug. 28, 2018 cited in PCT/US18/028491.

"Fittings and Flanges" (Hydraulics & Pneumatics) Jan. 31, 2005, http://www.hydraulicpneumatics.com/200/TechZone/FittingsCouplin/Article/False/9470/TechZone-Fittings Couplin; Figure 5.

* cited by examiner

+L Rotation    −L (R) Rotation

VERTEBRAL BODY MANIPULATION DEVICE AND METHODS

CROSS REFERENCE TO RELATED APPLICATIONS

This application is a Continuation of application Ser. No. 16/659,060, filed Oct. 21, 2019, which is a U.S. National Phase of International Patent Application No. PCT/US2018/028491 filed Apr. 20, 2018, which claims the benefit under 35 U.S.C. § 119 (e) of U.S. Provisional Application Ser. No. 62/488,347 filed Apr. 21, 2017, the disclosures of which are incorporated herein by reference in their entirety.

FIELD OF DISCLOSURE

The present disclosure relates to instruments and methods for stabilizing and manipulating the spine. More particularly, the present disclosure relates to a vertebral body manipulation instrument for use in connection with surgical treatment modalities for the spine.

BACKGROUND OF THE DISCLOSURE

Spinal deformity (e.g., spondylolithesis) often requires surgical correction. A common way to reduce spinal deformity is to use plier-type instruments. This generally requires multiple instruments and manipulations in different spatial planes to correct the spinal deformity. Unfortunately, fine control of such plier-type instruments may be difficult to achieve, especially while changing from one spatial plane to another. Additionally, such plier-type instruments are typically limited to open surgery. Disadvantageously, such instruments frequently use rods that are mounted over pedicle screws to operate, which constrains the maneuverability of the vertebral bodies, making it even more difficult to correct the spinal deformity. Another impediment of prior art instrumentation is that profiling or customizing the rods is often difficult to determine in advance of the surgical procedure. Thus, there is an urgent unmet need for new and improved vertebral body manipulation devices and methods to facilitate spinal surgeries that overcome the problems of prior art instruments described above.

SUMMARY OF THE DISCLOSURE

The present disclosure features a vertebral body manipulation device that is used in combination with a plurality of vertebral anchors, which may be any of a variety of vertebral anchors known to those skilled in the art (e.g., spinal pedicle screws and the like), to form a spinal implant system. Such a vertebral body manipulation instrument or device is configured and arranged so as to allow correction of the translation as well as application of distraction across a segment in an independent fashion. In further embodiments, such a vertebral body manipulation device or instrument embodies one or more identical modules that are configured as needed for correcting the deformity, and in more particular embodiments each instrument/device includes a plurality of such modules. Such a vertebral body manipulation device allows reorientation of the vertebral segment(s) as needed.

In further embodiments, each module includes two separate assemblies: a base unit that is configured and arranged so as to attach to a plurality of vertebral anchors and a vertebral body manipulation device that controls the movement of the module.

The vertebral body manipulation device is unique in that it may be used in combination with almost any currently available vertebral anchor. It may also be used with both "open" surgical procedures and percutaneous pedicle screw techniques. It allows a continuous adjustment and allows for manipulation of the vertebral segment to occur with intuitive uncoupled motion.

In further embodiments, the base unit includes two base elements, each base element including at least a threaded pole, a smooth pole, and a quick-lock mechanism at one end of the threaded and smooth poles. The quick-lock mechanism may be configured and arranged so as to mate with a spinal implant via a screw extension and pedicle screw. In exemplary embodiments, the quick-lock mechanism may be configured and arranged to mate with the screw extension connected to the spinal implant.

The threaded pole is threaded along its length and in further embodiments, such a pole is a tubular member. As described further herein, the thread surface of the threaded pole corresponds to the same thread surface as that embodied in the primary device and the primary device threads onto the threaded pole base. It is contemplated within the scope of the disclosure that the thread surface may lend a mechanical advantage that allows for the relative movement of the vertebral bodies.

In further embodiments, the primary device includes two portions that are connected to one another by two parallel sets of bars that are allowed to pivot in one plane around a central point forming a double 'X' configuration (e.g., a scissor mechanism). The primary device may be configured and arranged so as to separately control movement along the Anterior-Posterior (AP), Superior-Inferior (SI), and Left-Right (LR) directions of the Left-Posterior-Superior (LPS) patient coordinate system. Depending how the one or more modules are configured, placed, and oriented on the spine, the three DoF for each module can achieve a multi-degree of freedom correction (e.g., 5 or 6 DoF).

In exemplary, illustrative embodiments, the primary device or reduction instrument is mounted via a footlink to, for example, a DePuy Expedium Viper V2 extension and Expedium pedicle screw. The Expedium pedicle screw is a polyaxial screw, and during normal function it becomes rigid when locked to a rod in a rod screw construct as a result of the construct rod being forced by a nut into a bushing which results in the ball at the head of the screw being forced against the tulip of the screw, and thus by friction, constrains the screw. This mechanism can be engaged with the vertebral body manipulation instrument. The vertebral body manipulation device of the present disclosure works with all existing pedicle screw systems, from any manufacture, to convert a polyaxial screw to a functionally a screw.

According to further aspects, the present disclosure also features methods for stabilizing a spine using such an implant system and/or vertebral body manipulation device as described herein. Also featured are methods for treating spondylolithesis using surgical techniques and using the vertebral body manipulation device and/or implant system of the present disclosure. Such methods are usable with both "open" surgical procedures and percutaneous pedicle screw techniques. Such methods further include continuous adjustment and manipulation of the vertebral segment to occur with intuitive uncoupled motion.

As the vertebral body manipulation device of the present disclosure embodies a mechanism or quick-lock mechanism for coupling the instrument to any currently available spinal implant utilizing a plurality of vertebral anchors as the implant, such a vertebral body manipulation device is easily adaptable to use with such an implant. Thus, a vertebral body manipulation device of the present disclosure would not require redesign of a current implant or vertebral anchor.

In an aspect, a vertebral body manipulation instrument according to the disclosure may include: at least one module including a first base unit, a second base unit, a threaded pole, a smooth pole, and a scissors mechanism; the first base unit having an upper end connected to the threaded pole and a lower end configured to mate with a first vertebral anchor; the second base unit having an upper end connected to the smooth pole and a lower end configured to mate with a second vertebral anchor; and the scissors mechanism connecting the first base unit to the second base unit and the threaded pole to the smooth pole.

In an embodiment, the scissors mechanism connects to the first base unit and the second base unit via a revolute joint.

In an embodiment, the scissors mechanism connects to the threaded pole via a revolute joint mounted on a threadable coupling configured to interface with a threaded portion of the threaded pole.

In an embodiment, the scissors mechanism connects to the smooth pole via a revolute joint mounted on a slidable coupling configured to interface with a smooth portion of the smooth pole.

In an embodiment, the vertebral manipulation instrument is able to convey three degrees of freedom of movement to the first and second vertebral anchors when the lower end of the first base unit is mated with the first vertebral anchor and the lower end of the second base unit is mated with the second vertebral anchor.

In an embodiment, the first base unit and the second base unit each have a quick-lock mechanism configured to secure the first and second vertebral anchors. In an embodiment, the threadable coupling includes a rotary joint. In an embodiment, the threadable coupling includes a nut and a nut cage configured to interface with a plurality of grooves on the threaded pole and a plurality of bearing balls positioned between the threaded coupling and the nut cage, the nut including a recessed thread configured to provide clearance relative to the plurality of grooves on the threaded pole.

In an aspect, the disclosure provides a method for surgical treatment of spondylolithesis comprising the step(s) of: providing the vertebral manipulation instrument of claim 1, wherein each of the at least one modules is configured and arranged to cause translation or rotation of a vertebral segment along an Anterior-Posterior (AP), Superior-Inferior (SI), and/or Left-Right (LR) axis of a Left-Posterior-Superior (LPS) patient coordinate system. In an embodiment, the method further includes the step(s) of: securing the manipulation instrument to a spine using spinal pedicle screw instrumentation.

In an aspect, the disclosure provides a surgical manipulation instrument, that includes at least one module including a first base unit, a second base unit, a threaded pole, a smooth pole, and a scissors mechanism; the first base unit having an upper end connected to the threaded pole and a lower end configured to mate with a first vertebral anchor; the second base unit having an upper end connected to the smooth pole and a lower end configured to mate with a second vertebral anchor; and the scissors mechanism connecting the first base unit to the second base unit and the threaded pole to the smooth pole, wherein the scissors mechanism confers three degrees of freedom of movement to the first and second vertebral anchors when the lower end of the first base unit is mated with the first vertebral anchor and the lower end of the second base unit is mated with the second vertebral anchor.

In an embodiment, the scissors mechanism connects to the threaded pole via a revolute joint mounted on a threadable coupling configured to interface with a threaded portion of the threaded pole.

In an embodiment, the threadable coupling is operated with a wrench or a torque wrench.

In an embodiment, the scissor mechanism is configured to reduce changes in mechanical advantage.

In an embodiment, the instrument is configured to maintain a head of the first vertebral anchor at the same relative orientation and level of a head of the second vertebral anchor.

In an embodiment, the instrument is configured to adjust the distance between the head of the first vertebral anchor and the head of the second vertebral anchor.

In an embodiment, the instrument is configured to manipulate one or more vertebral bodies by applying a rocking and/or twisting motion to the first and/or second vertebral anchors which have been anchored in the one or more vertebral bodies.

In an aspect, the disclosure provides a fastener that includes: a nut having a threaded inner surface and an outer surface including at least one circumferential nut guide; and a sleeve configured to rotatably interface with the at least one circumferential nut guide.

In an embodiment, the sleeve has an inner surface including at least one circumferential sleeve guide configured to align with the at least one circumferential nut guide.

In an embodiment, the at least one circumferential nut guide houses a plurality of ball bearings when aligned with the at least one circumferential nut guide.

In an embodiment, the sleeve maintains a fixed position when the nut is rotated.

In an embodiment, an outer surface of the sleeve is configured to attach a revolute joint.

In an aspect, the disclosure provides a one degree of freedom (DoF) of movement device that includes: a first support member having a first end and a second end, wherein a distal portion of the first end is threaded and the second end includes a fixed mounting portion; a second support member having a first end and a second end wherein a distal portion of the first end is smooth and the second end includes a fixed mounting portion; a threaded coupling configured to mate with the threaded first end of the first support member; a slidable coupling configured to slidably engage with the smooth first end of the second support member; a first crossbar; a second crossbar; and at least five revolute joints, wherein a first revolute joint couples a first end of the first crossbar to the threaded coupling, a second revolute joint couples a second end of the first crossbar to the fixed mounting portion of the second support member, a third revolute joint couples a first end of the second crossbar to the slidable coupling, a fourth revolute joint couples a second end of the second crossbar to the fixed mounting portion of the first support member, and a fifth revolute joint couples the first crossbar to the second crossbar, wherein the at least five revolute joints confer one DoF of movement to the device.

In an aspect, the disclosure provides a vertebral body manipulation instrument (VBMI), including: a first support member having a first end and a second end, wherein a distal portion of the first end is threaded and the second end includes a fixed mounting portion and is configured to attach to a first vertebral anchor; a second support member having a first end and a second end wherein a distal portion of the first end is smooth and the second end includes a fixed mounting portion and is configured to attach to a second vertebral anchor; a threaded coupling configured to mate with the threaded first end of the first support member; a slidable coupling configured to slidably engage with the smooth first end of the second support member; a first crossbar; a second crossbar; and at least five revolute joints, wherein one revolute joint connects a middle portion of the first crossbar to a middle portion of the second crossbar to form a X-shaped structure in which the first crossbar spans between the threaded coupling and the fixed mounting portion of the second support member and the second crossbar spans between the slidable coupling and the fixed mounting portion of the first support member, and the VBMI is configured to maintain a head of the first vertebral anchor at the same relative orientation and level of a head of the second vertebral anchor. In an embodiment, the instrument is configured to adjust the distance between the head of the first vertebral anchor and the head of the second vertebral anchor. In an embodiment, the instrument is configured to manipulate one or more vertebral bodies by applying a rocking and/or twisting motion to the first and/or second vertebral anchors which have been anchored in the one or more vertebral bodies.

In an aspect, the disclosure provides a method of manipulating at least one vertebral body, including the steps of placing a first vertebral anchor in a first vertebral body; placing a second vertebral anchor in a second vertebral body; attaching a vertebral manipulation device to a head portion of the first vertebral anchor and a head portion of the second vertebral anchor; and maintaining, while manipulating at least one vertebral body, the head portion of the first vertebral anchor at the same relative orientation and level as the head portion of the second vertebral anchor. In an embodiment, manipulating the at least one vertebral body occurs by applying a rocking and/or twisting motion to the first and/or second vertebral anchors.

Other aspects and embodiments of the disclosure are discussed below.

Definitions

The instant disclosure is most clearly understood with reference to the following definitions:

As used in the specification and claims, the singular form "a," "an," and "the" include plural references unless the context clearly dictates otherwise.

As used herein, the term "comprising" or "including" is intended to mean that the compositions, methods, devices, apparatuses and systems include the recited elements, but do not exclude other elements. "Consisting essentially of," when used to define compositions, devices, apparatuses, systems, and methods, shall mean excluding other elements of any essential significance to the combination. Embodiments defined by each of these transition terms are within the scope of this disclosure.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

BRIEF DESCRIPTION OF THE DRAWINGS

For a fuller understanding of the nature and desired objects of the present disclosure, reference is made to the following detailed description taken in conjunction with the accompanying drawing figures wherein like reference character denote corresponding parts throughout the several views and wherein.

DETAILED DESCRIPTION OF THE DISCLOSURE

Figure 1A:
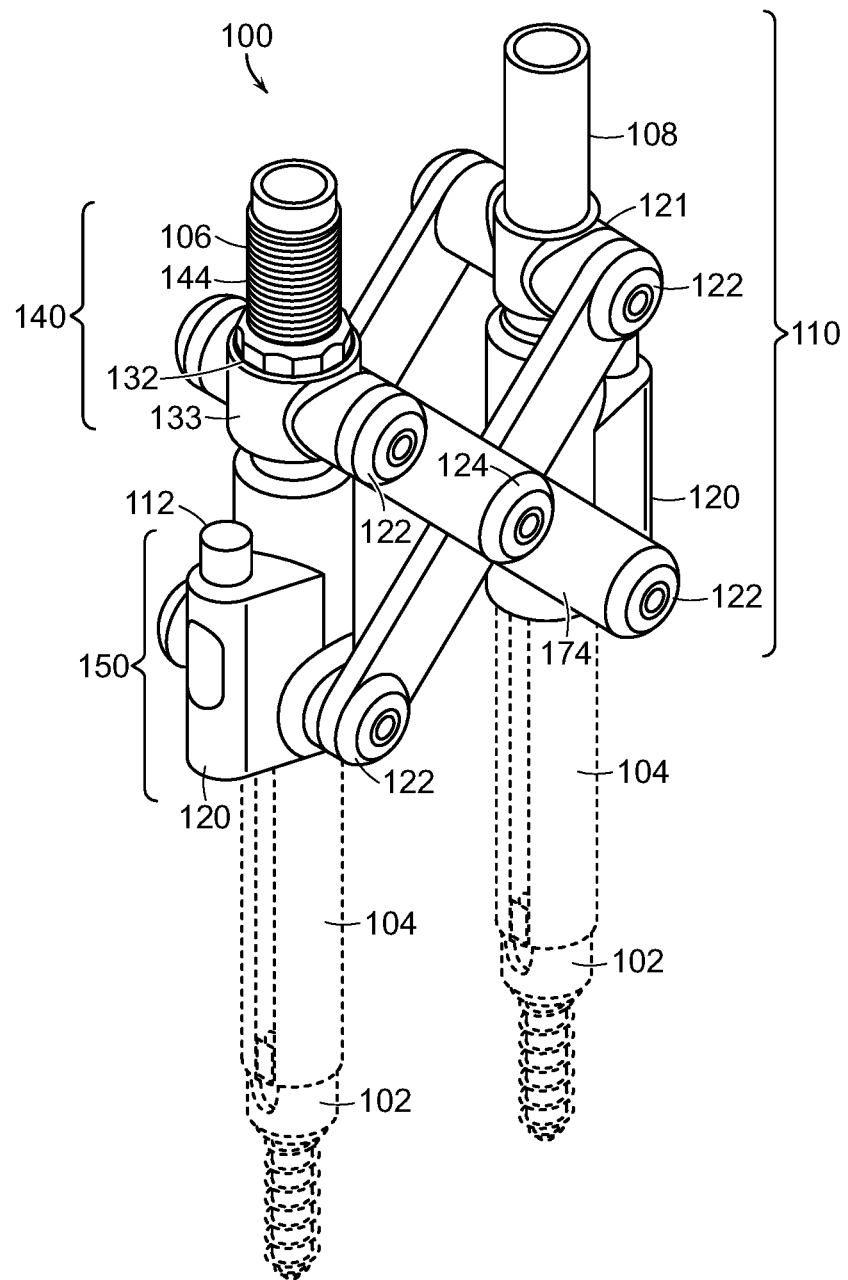
FIG. 1A is a perspective view of a vertebral body manipulation device according to an exemplary embodiment of the present disclosure.

The present disclosure features a vertebral body manipulation device that is simpler, smaller, and provides more degrees of freedom (DoF) of movement than currently available instrumentation. The vertebral body manipulation device of the present disclosure is based, at least in part, on the discovery that incorporating both a threaded connection joint and a smooth connection joint into a scissor mechanism having an X configuration may provide a module having one DoF of maneuverability in and of itself. Moreover, the vertebral body manipulation device of the present disclosure may provide five or six DoF of maneuverability relative to the heads of the vertebral anchors to which it is attached when used in pairs of two or more devices. Advantageously, the present device provides two pin connection joints within the scissor mechanism having an X configuration that may be connected directly to quick-lock mechanisms configured to mate with a screw extension and/or vertebral anchor, which provides a more compact design that also has the benefit of keeping the heads of the vertebral anchors (e.g., pedicle screws) aligned and thereby facilitates placement of a rod. The heads of the screws are oriented towards one another and at the same level which guarantees the placement of a straight rod over the heads, without the need to profile or adjust it. Additionally, the threaded connection joint reduces internal friction of the mechanism, thereby enhancing the force-feedback of the device and providing the surgeon with a better representation of the forces exerted by the device on the vertebral bodies.

Abnormal curvature of the spine is referred to as spinal deformity, one of the oldest and most common diseases [Heary R F, Madhavan K: *Neurosurgery*. September 2008; Vol. 63(3 Suppl) pp. 5-15]. The causes of spinal deformity are numerous and may include congenital, degenerative, neoplastic, infectious, traumatic, iatrogenic and idiopathic etiologies [Watters W C, et al., *Spine J*. July 2009; Vol. 9(7) pp. 609-614]. Spondylolisthesis is a form of spinal deformity commonly associated with degenerative spondylosis. The deformity usually occurs in the lumbar and sacral regions of the spine and may affect sagittal balance [Barrey C, et al., *European Spine Journal*. September 2007; Vol. 16(9) pp. 1459-1467, El-Rich M A C, et al. *Stud Health Technol Inform*. 2006; Vol. 123 pp. 341-344, Labelle H, et al., *Spine* (Phila Pa 1976). Mar. 15, 2005; Vol. 30(6 Suppl) pp. S27-34, and Barrey C, et al., *Eur Spine J*. September 2007; Vol. 16(9) pp. 1459-1467]. Spondylolisthesis is the anterior subluxation of one vertebral body on another, usually L5 on S1, or L4 on L5. Spinal deformity, including scoliosis, occurs frequently and may be as high as 68% in elderly populations [Ailon T, et al., *Neurosurgery*. October 2015; Vol. 77 Suppl 4 pp. S75-91]. Spondylolisthesis occurs in about 5.8% of men and 9.1% of women, with many cases being asymptomatic [Ettinger B, et al., *J Bone Miner Res*. April 1992; Vol. 7(4) pp. 449-456 and Schwab F, et al., *Spine* (Phila Pa 1976). May 1, 2005; Vol. 30(9) pp. 1082-1085]. Spondylolisthesis can cause neurological deficit from neural compression.

Surgical treatment for spondylolisthesis usually involves laminectomy to decompress the neural elements, maneuvers to re-align sagittal and/or coronal balance, and arthrodesis to hold the new alignment [Hresko M T, et al., *Spine* (Phila Pa 1976). Sep. 15, 2007; Vol. 32(20) pp. 2208-2213 and Kepler C K, et al., *Orthop Surg*. February 2012; Vol. 4(1) pp. 15-20]. To accomplish the realignment, a reduction with pedicle screws followed by interbody fusion with posterolateral fusion is commonly performed. The fixation is commonly done with implanted pedicle screws and titanium rods attached to the screws. The reduction is achieved with superior-inferior (SI) and anterior-posterior (AP) actions to create distraction-compression and subluxation-slippage translation of the vertebral bodies, respectively. Multiple studies have compared treatment approaches [Slone R M, et al., *Radiographics*. May 1993; Vol. 13(3) pp. 521-543, and Weinstein et al., *N Engl J Med*. May 31, 2007; Vol. 356(22) pp. 2257-2270], and clinical guidelines for spondylolisthesis have been developed by the North American Spine Society (NASS) [Watters W C, et al., *Spine J*. July 2009; Vol. 9(7) pp. 609-614], offering guidance to clinicians when encountering this pathology.

The instrumentation currently available for reduction takes the shape of pliers. This often requires multiple instruments (for example for distraction or compression) and steps to achieve the correction, making the procedure technically challenging and difficult to maintain, especially while changing from one instrument or maneuver to another. The pliers also require the rods to be placed between the pedicle screw heads before the correction. Unfortunately, this limits the ability to maneuver the vertebral bodies.

Moreover, these devices have been developed for the classic open surgery. The ability to correct deformities and perform the operations with minimally invasive percutaneous techniques [Chrastil J, Patel A A: J Am Acad Orthop Surg. May 2012; Vol. 20(5) pp. 283-291, Kasliwal M K, et al., J Neurosurg Spine. August 2012; Vol. 17(2) pp. 128-133, Ogilvie J W: Spine (Phila Pa 1976). Mar. 15, 2005; Vol. 30(6 Suppl) pp. S97-101, Quraishi N A, et al., European Spine Journal. Dec. 19, 2012., Sansur C A, et al. J Neurosurg Spine. November 2010; Vol. 13(5) pp. 589-593, Smith J S, et al., Spine (Phila Pa 1976). Nov. 1, 2012; Vol. 37(23) pp. 1975-1982, Smith J S, et al., Spine (Phila Pa 1976). May 20, 2011; Vol. 36(12) pp. 958-964. Chen L, et al, Chin Med J (Engl). January 2003; Vol. 116(1) pp. 99-103, Kasliwal M K, et al. Neurosurgery. July 2012; Vol. 71(1) pp. 109-116, Tian N F, Xu H Z: IInt Orthop. August 2009; Vol. 33(4) pp. 895-903, Fu T S, et al., Int Orthop. August 2008; Vol. 32(4) pp. 517-521, Schlenk R P, et al., Neurosurg Focus. Jan. 15, 2003; Vol. 14(1) pp. e2] has improved and was made possible by intraoperative fluoroscopic and computed tomography (CT) image guidance [Tian N F, Xu H Z: IInt Orthop. August 2009; Vol. 33(4) pp. 895-903 and Fu T S, et al., Int Orthop. August 2008; Vol. 32(4) pp. 517-521]. However, instruments to correct the deformity using minimally invasive procedures are limited and plier-type instruments are normally unsuitable for these procedures.

In general, forces required to correct spinal deformity are largely unknown [Schlenk R P, et al., *Neurosurg Focus*. Jan. 15, 2003; Vol. 14(1) pp. e2]. It is therefore likely that these are highly variable between different surgical techniques and among surgeons. Correction forces are exerted on the screws and respectively on the vertebral bodies during the operation, and excessive loads may lead to bone fracture. Moreover, these forces may be falsely perceived by the surgeon, due to limitations of the instruments used. Current deformity correction devices lack this capability. The vertebral body manipulation device described herein presents several advantages over currently available instrumentation.

Figure 1B:
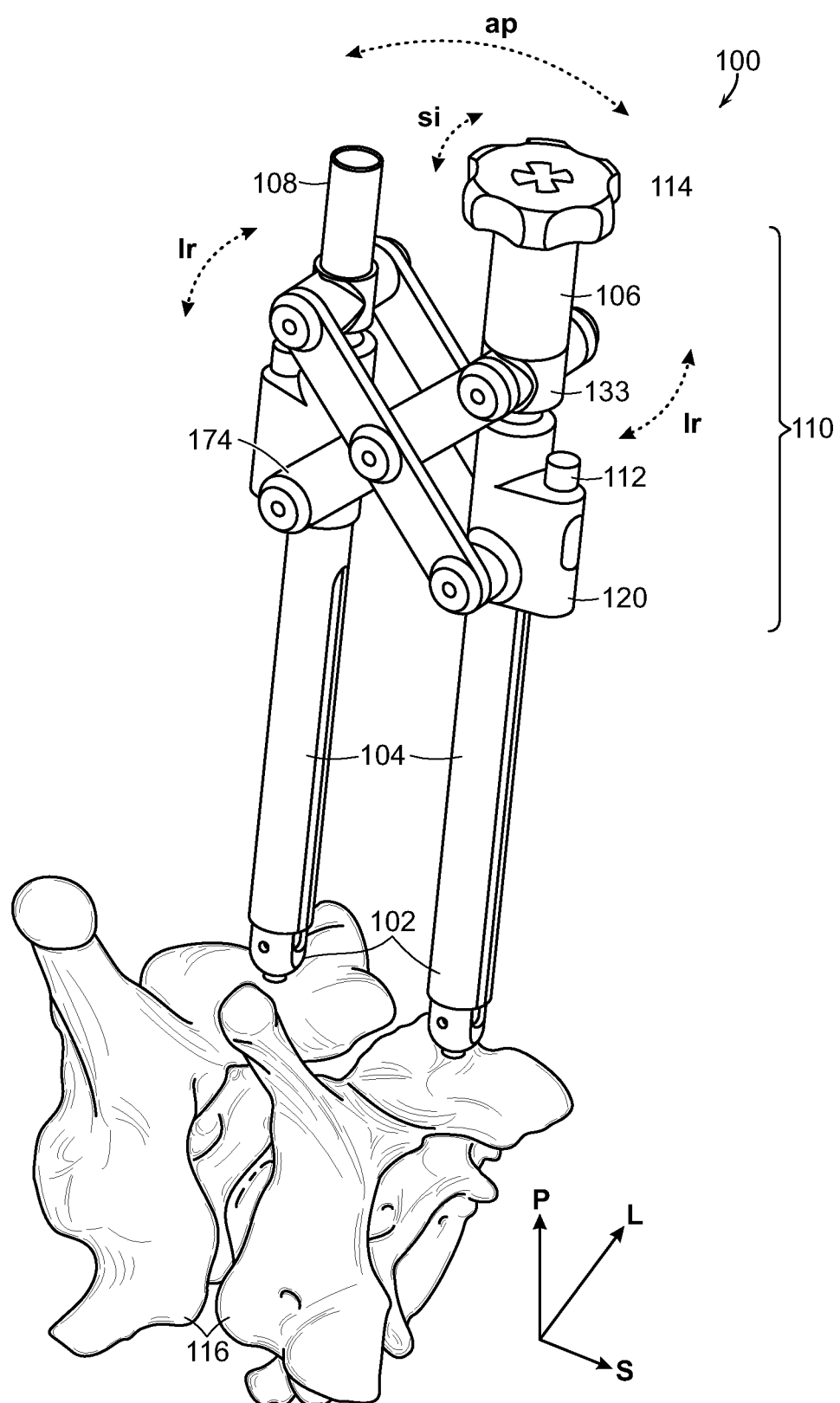
FIG. 1B is a perspective view of a vertebral body manipulation device attached to vertebral bodies according to an exemplary embodiment and further illustrating the orthogonal translations capable by such an instrument. The Left-Posterior-Superior (LPS) patient coordinate system is also shown, together with the arrows describing the maneuverability that the device provides in the LPS directions.

Referring now to the various figures of the drawing wherein like reference characters refer to like parts, there are shown in FIG. 1A and FIG. 1B illustrative views of a vertebral body manipulation device 100 of the present disclosure.

FIG. 1A shows an exemplary vertebral body manipulation device 100 according to the disclosure, which includes a module 110 having two base units 120, which may be interconnected by a scissor mechanism 174 having an X configuration (e.g., a scissor X mechanism). Base unit 120 may include a quick-lock mechanism 150 configured to allow base unit 120 to attach to a screw extension 104, which may in turn be configured to attach to a pedicle screw 102. Quick-lock mechanism 150 also includes button 112 which engages the quick-lock mechanism 150, described in detail below.

Scissor X mechanism 174 may include four revolute joints 122 and a central joint 124. Two of the four revolute joints 122 may be mounted to a base unit 120, one of the revolute joints 122 may be mounted to threaded coupling 133, and one of the revolute joints 122 may be mounted to slidable coupling 121. Threaded coupling 133 may be configured to mate with threaded pole 106, while slidable coupling 121 may be configured to mate with and slidably engage smooth pole 108. Threaded pole 106 includes a nut assembly 140, described further below, which includes a nut 132 and a threaded surface 144. In general terms, the combination of threaded pole 106 with a base unit 120 may be considered as a first support member, while the combination of smooth pole 108 with a base member 120 may be considered as a second support member.

FIG. 1B depicts vertebral body manipulation device 100 attached to vertebral bodies 116. Wrench 114 may be placed on the threaded pole 106 of the vertebral body manipulation device 100 and configured to manipulate threaded coupling 133 of scissor X mechanism 174 up or down threaded pole 106 (hidden from view under wrench 114) to operate the device. In some embodiments, wrench 114 may be a torque wrench. Anterior-Posterior (AP), Superior-Inferior (SI), and Left-Right (LR) axes are labeled. Smooth pole 108 may be configured to engage to scissor X mechanism 174 via any of a variety of slidable coupling configurations. Threaded pole 106 may be configured to engage with base unit 120, which also includes button 112.

In embodiments, vertebral body manipulation device 100 provides a method of manipulating at least one vertebral body, that includes the steps of placing a first vertebral anchor in a first vertebral body; placing a second vertebral anchor in a second vertebral body; attaching a vertebral manipulation device to a head portion of the first vertebral anchor and a head portion of the second vertebral anchor; and maintaining, while manipulating at least one vertebral body, the head portion of the first vertebral anchor at the same relative orientation and level as the head portion of the second vertebral anchor.

In embodiments, screw extension 104 and pedicle screw 102 may be any of a variety of commercially available screw extensions and pedicle screws. Alternatively, a screw extension 104 could be specifically designed to manipulate pedicle screw 102 in conjunction with the vertebral body manipulation device 100.

As the vertebral body manipulation device and functionalities thereof are intended for use with a body, the materials shall be any of a number of bio-compatible materials presently known or hereinafter developed. Such materials also shall be suitable for the forces and loads that can occur during usage of the instrument. In addition, while particular shapes or geometries are described herein, it is within the scope of the present disclosure for other shapes or geometries to be used as long as the described translational and rotational functional aspects can be carried out using such shapes or geometries.

The modules 110 for such a vertebral body manipulation device 100 are configured and arranged as needed for correcting the deformity. As described in further detail herein, each module has three DoF with uncoupled orthogonal translations, and may provide five or six DoF when used in combinations of two or more modules 110.

Vertebral body manipulation device is unique in that it may be used in combination with almost any of a number of currently available vertebral anchors (e.g., spinal pedicle screw instrumentation). It also is usable with both "open" surgical procedures and percutaneous pedicle screw techniques. It allows for continuous adjustment and allows for manipulation of the vertebral segment to occur with an intuitive uncoupled motion.

Figure 2:
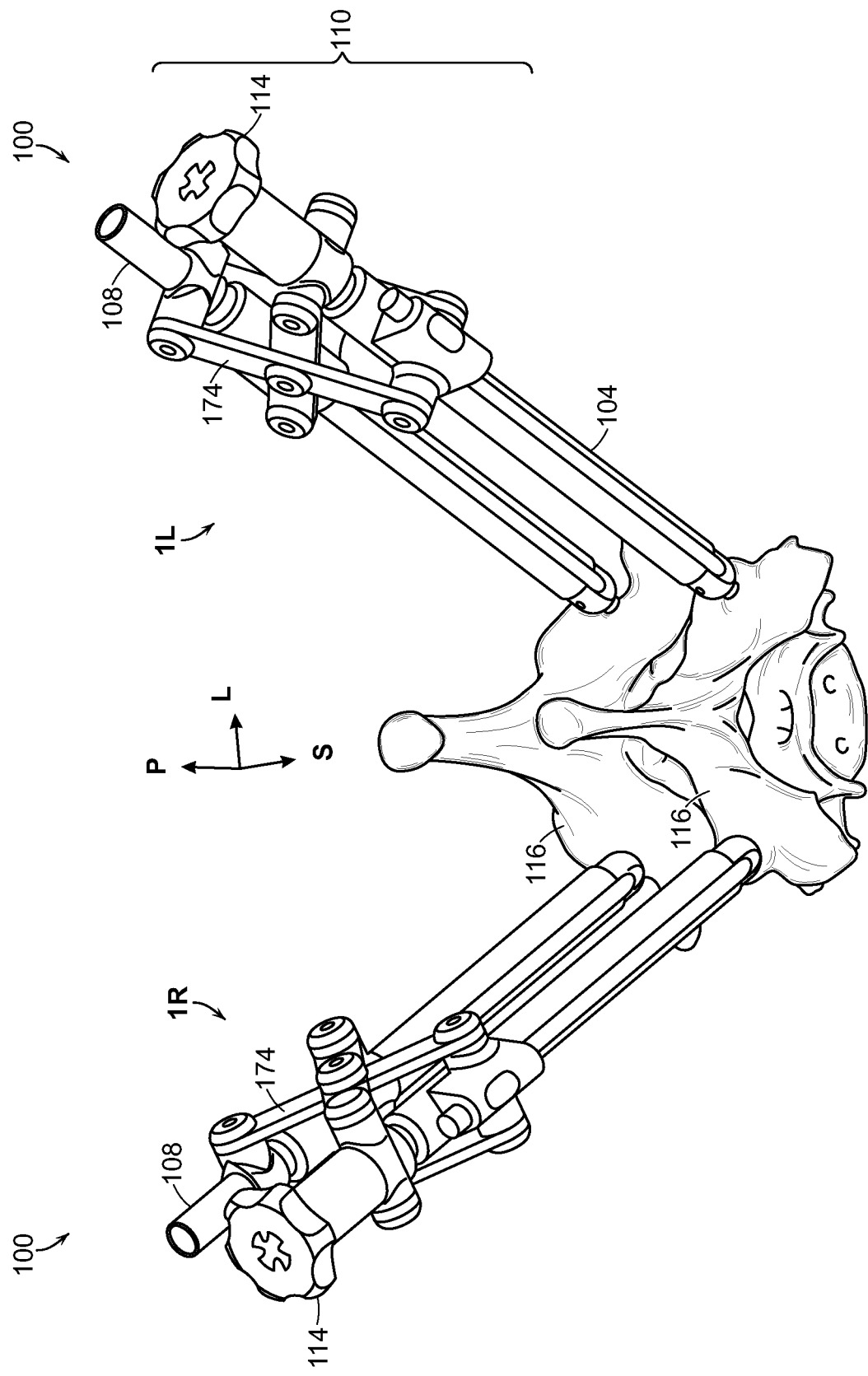
FIG. 2 is an illustrative view of two devices used to manipulate a pair of vertebral bodies, one on each side (left and right) of the spine device according to an exemplary embodiment of the present disclosure.

As depicted in FIG. 2, a plurality of vertebral body manipulation devices 100 may be used. In particular embodiments, two vertebral body manipulation devices 100 are typically used to manipulate vertebral bodies 116, one on each side (left and right) of the spine. When used in combinations of two or more modules 110, the vertebral body manipulation device 100 of the present disclosure may provide five or six DoF of maneuverability when used.

Figure 3:
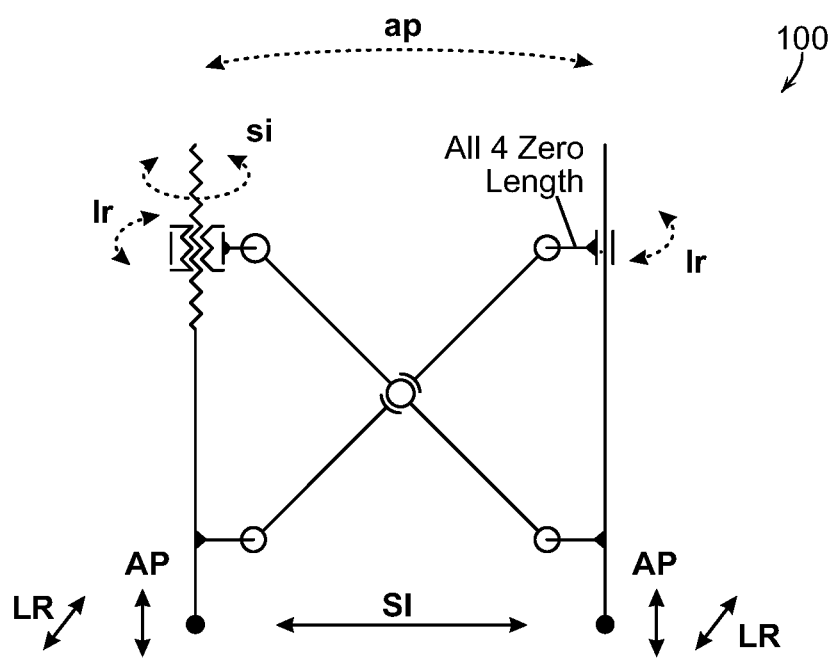
FIG. 3 is a kinematic diagram of the vertebral body manipulation device according to an exemplary embodiment of the present disclosure and its 3. DoF operation. Anterior-Posterior (AP), Superior-Inferior (SI), and Left-Right (LR) directions of the Left-Posterior-Superior (LPS) patient coordinate system are labeled.

FIG. 3 depicts a kinematic diagram illustrating the orthogonal translations capable according to the vertebral body manipulation device instrument of the present disclosure. As described herein, operation of the vertebral body manipulation device 100 provides 3 degrees of freedom (DoF) of relative maneuverability between the heads of the screws 102 to which it is attached, as shown in FIG. 2. The DoF are in the Anterior-Posterior (AP), Superior-Inferior (SI), and Left-Right (LR) directions of the Left-Posterior-Superior (LPS) patient coordinate system, represented in FIG. 1B and FIG. 3. The DoF provided by one device are:

SI maneuverability for either distraction or compression is achieved by spinning the nut (si).

AP maneuverability in either direction is performed by rocking the entire device in a quasi-sagittal plane as shown by the (ap) arrow.

LR maneuverability in either direction is performed by rotating the device in a quasi-coronal plane as shown by the (lr) arrow.

A novel aspect of the kinematics of vertebral body manipulation device 100 described herein, relative to prior art instruments (e.g., X-Press), is that the vertebral body manipulation device 100 maintains the heads the pedicle screws 102 parallel and at the same level. Unlike all other prior art devices, this ensures that a straight bar may be connected between the heads and eliminates the need to bend the bar prior to locking it in the pedicle screws 102 (not shown in FIG. 3), which is often the case with prior art tools.

Figure 4:
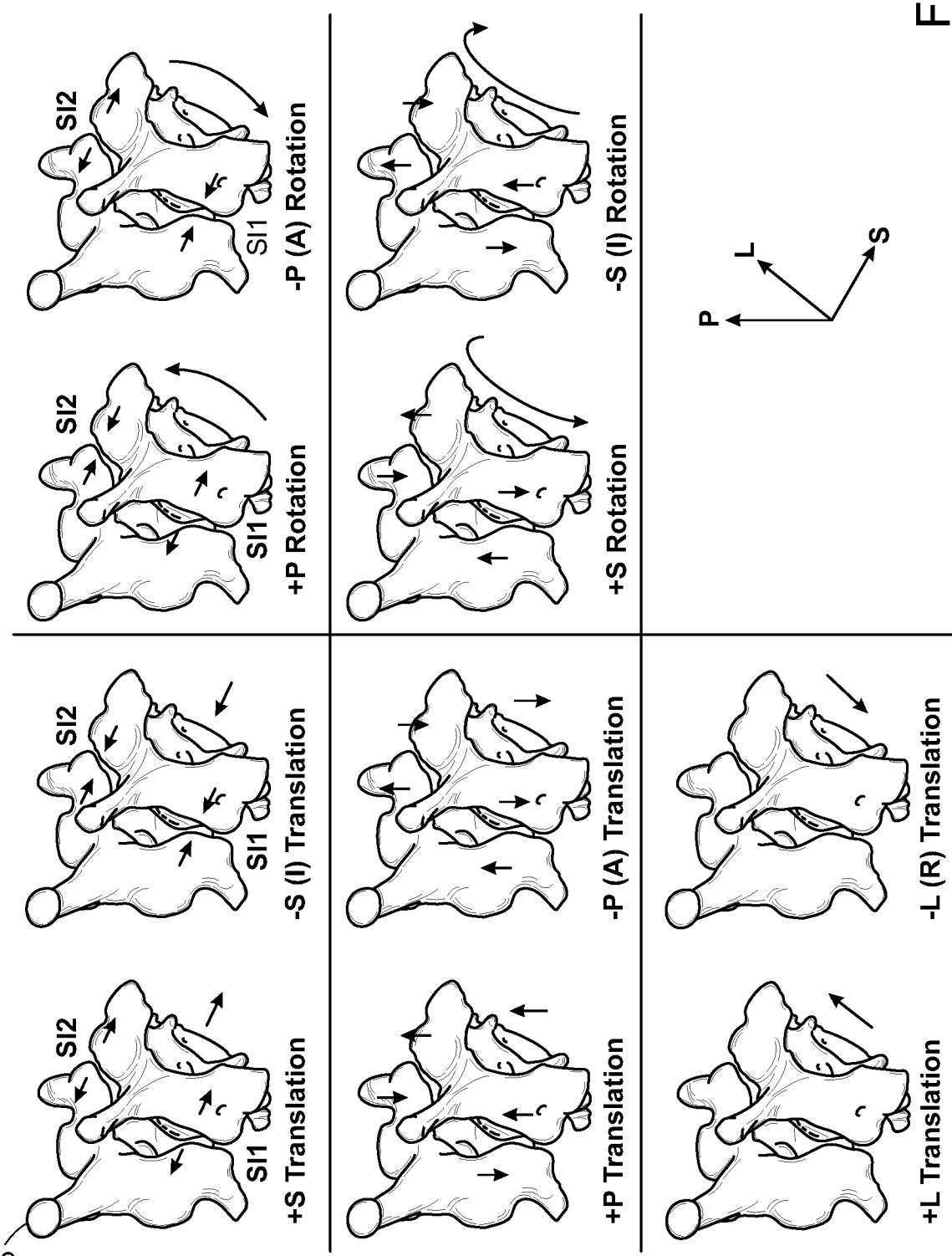
FIG. 4 is an illustrative view of the five DoF of relative maneuverability between the vertebral bodies provided by the vertebral body manipulation device according to an exemplary embodiment of the present disclosure. Translations/rotations relative to the AP, SI, and LR directions of the LPS patient coordinate system are shown.
Figure 5:
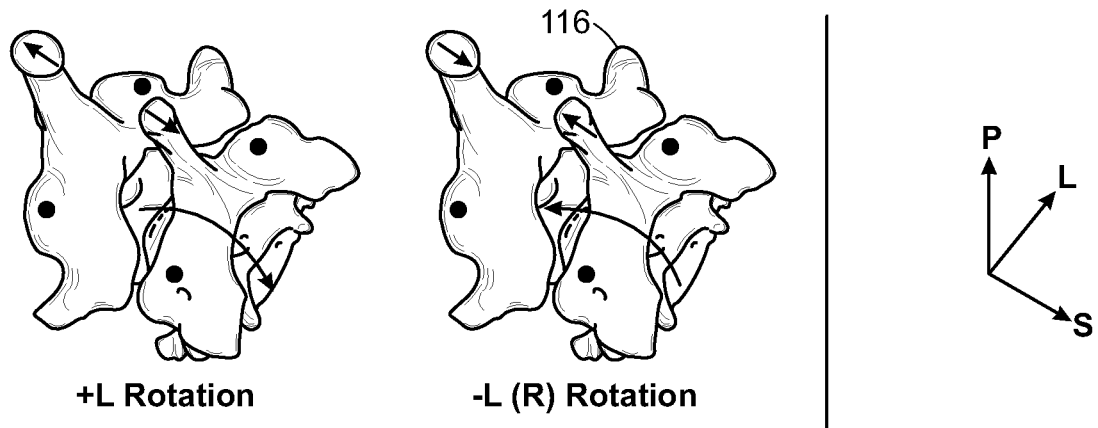
FIG. 5 is an illustrative view of the sixth DoF of relative maneuverability between the vertebral bodies provided by the vertebral body manipulation device according to an exemplary embodiment of the present disclosure. Rotations relative to the LR directions of the LPS patient coordinate system are shown.

The DoF of relative maneuverability between the vertebral bodies enabled by vertebral body manipulation devices 100 are presented in FIGS. 4 and 5. As shown in FIG. 4, two vertebral body manipulation devices 100 provide 5 DoF of maneuverability. For example, vertebral body manipulation devices 100 may provide +S translation and −S (I) translation, +P rotation and −P (A) rotation, +P translation and −P (A) translation, +S rotation and −S (I) rotation, and +L translation and −L (R) translation with respect to the LPS axes shown in the lower right section of FIG. 4. The mobility of the vertebral bodies 116 about these axes depends on multiple factors that include their current positioning and the properties of interconnecting tissues and disks. The controls of the devices are determined with fine adjustments in surgery, typically performed under X-Ray fluoroscopy guidance.

The positioning of the vertebral bodies in response the controls of the vertebral body manipulation devices 100 is also influenced by the state of the pedicle screws 102. On most pedicle screws 102 the head of the screw is mounted with a spherical joint 178. This spherical joint 178 may be locked or unlocked (poly-axial). Pedicle screw 102 head locking could be used to facilitate the maneuvers, for example the ±S Translations in FIG. 4.

In the DoF analysis of FIG. 4, the only missing DoF is the rotation about the L axis. This could be provided if the pedicle screw 102 are unlocked, the vertebral body manipulation devices 100 are maintained in position, and additional maneuvers are exerted with traditional instruments, for example on the spinous process, as shown in FIG. 5.

FIG. 5 depicts the 6$^{th}$ relative DoF of maneuverability between the vertebral bodies 116 may be achieved by holding the location of the unlocked pedicle screws 102 heads with the vertebral body manipulation device 100 and maneuvering the vertebral bodies 116, for example between the spinous process.

Vertebral Body Manipulation Device

Figure 6A:
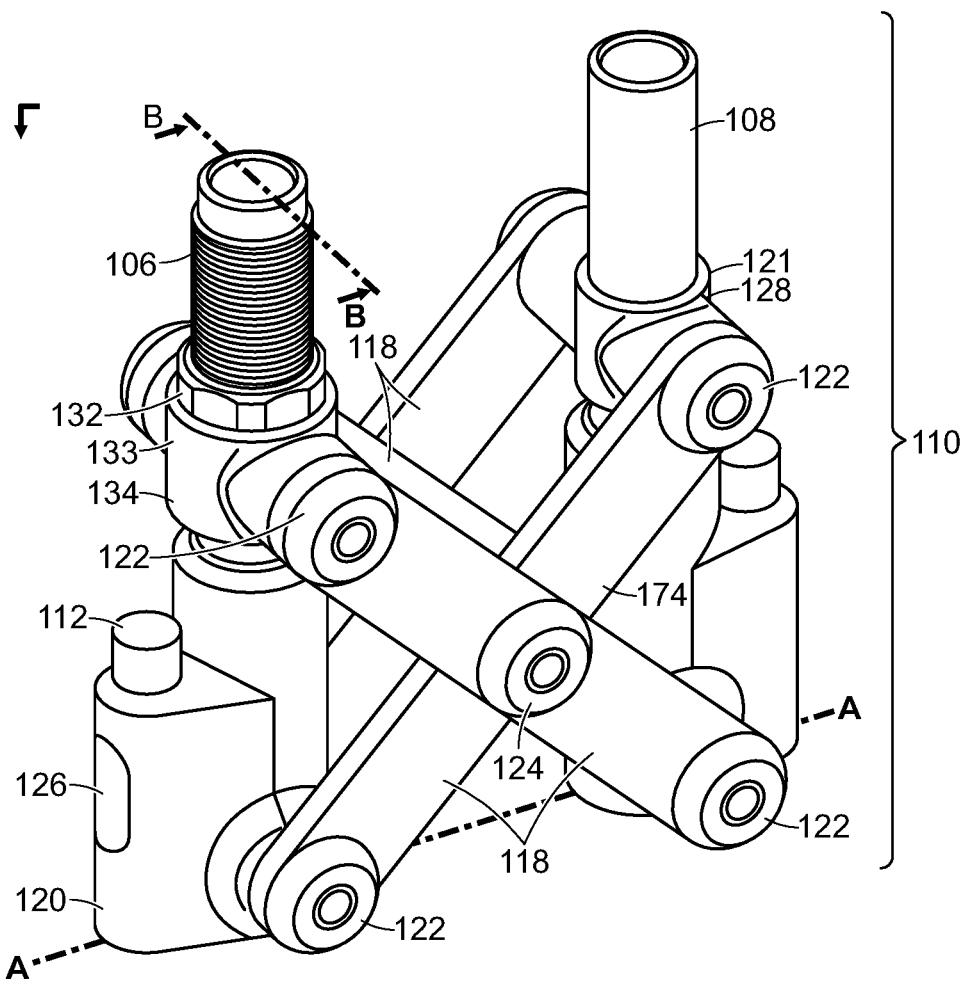
FIG. 6A is a perspective view of a module of the vertebral body manipulation device according to an exemplary embodiment of the present disclosure.
Figure 6B:
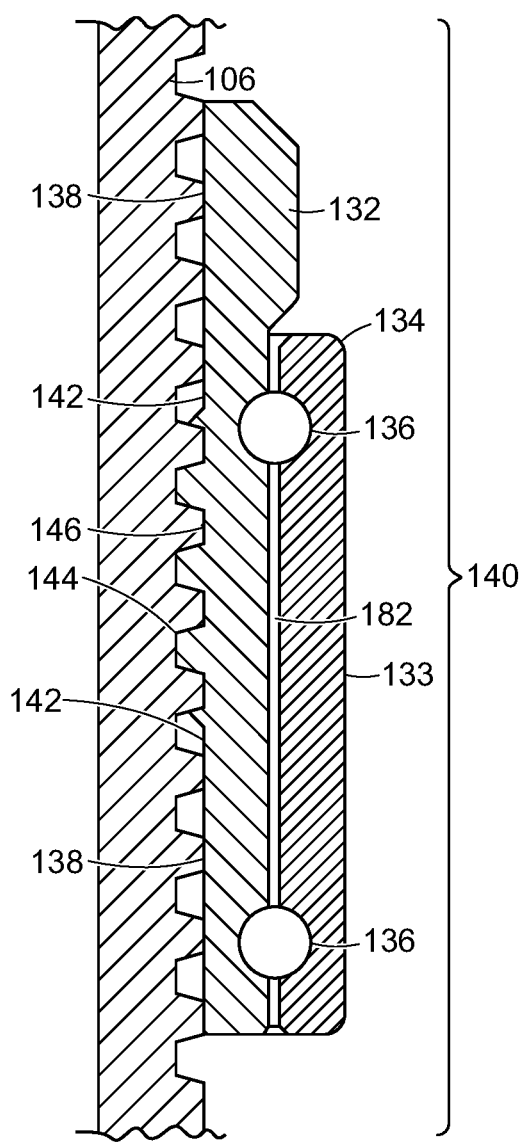
FIG. 6B is a cross-sectional view of a nut assembly coupled to a threaded pole of the vertebral body manipulation device according to an exemplary embodiment of the present disclosure.
Figure 6C:
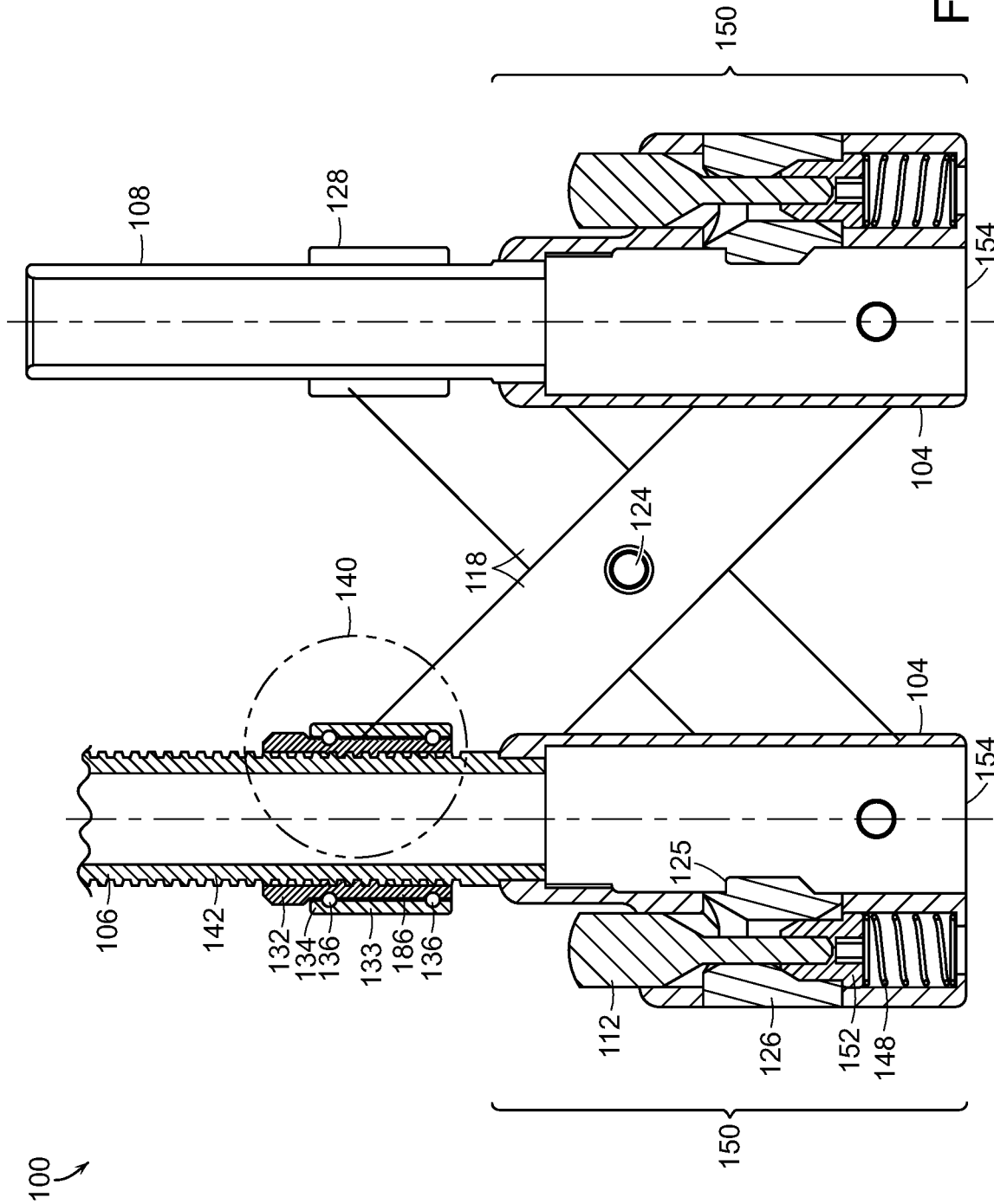
FIG. 6C is a cross-sectional view of a module of the vertebral body manipulation device according to an exemplary embodiment of the present disclosure.
Figure 6D:
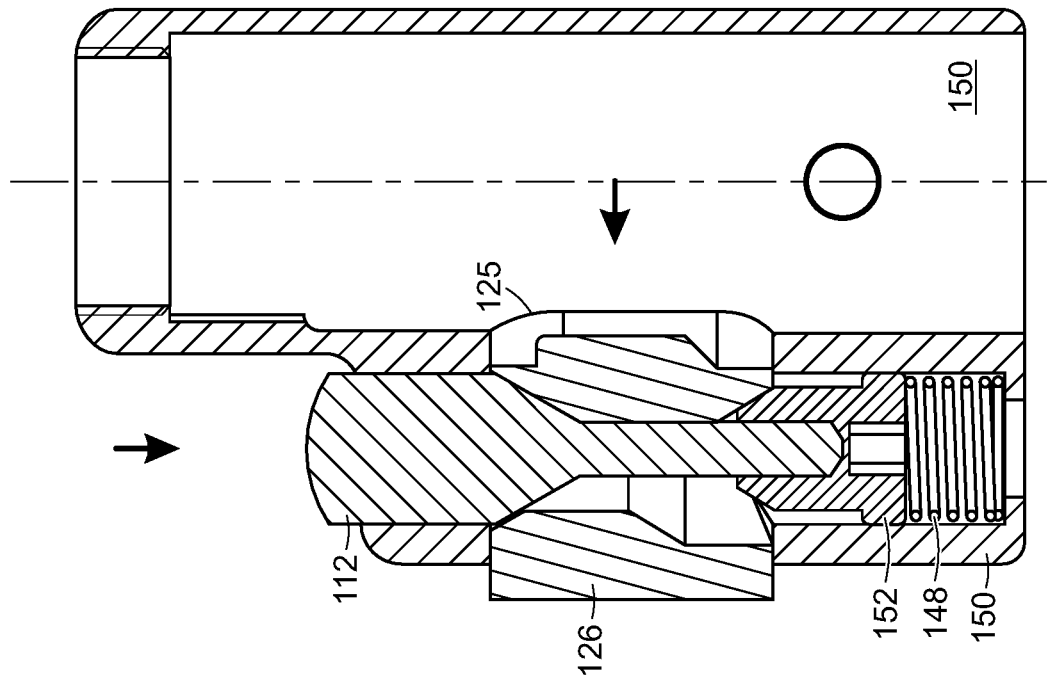
FIG. 6D is a cross-sectional view of a quick-lock mechanism of the vertebral body manipulation device in a closed (left panel) and opened (right panel) position according to an exemplary embodiment of the present disclosure.
Figure 6D:
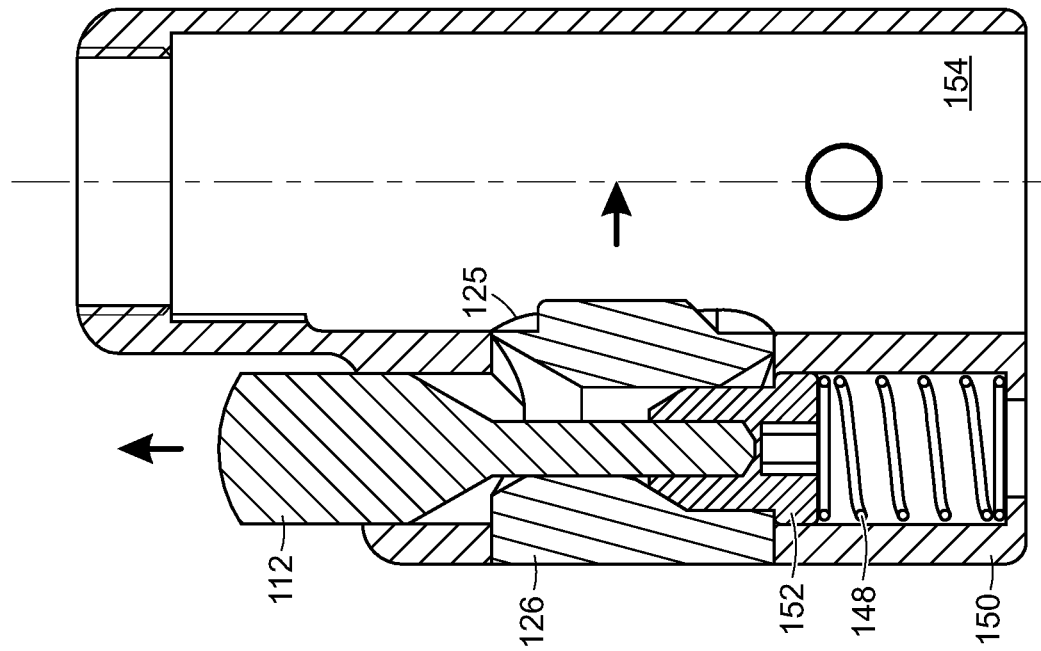
Figure 6E:
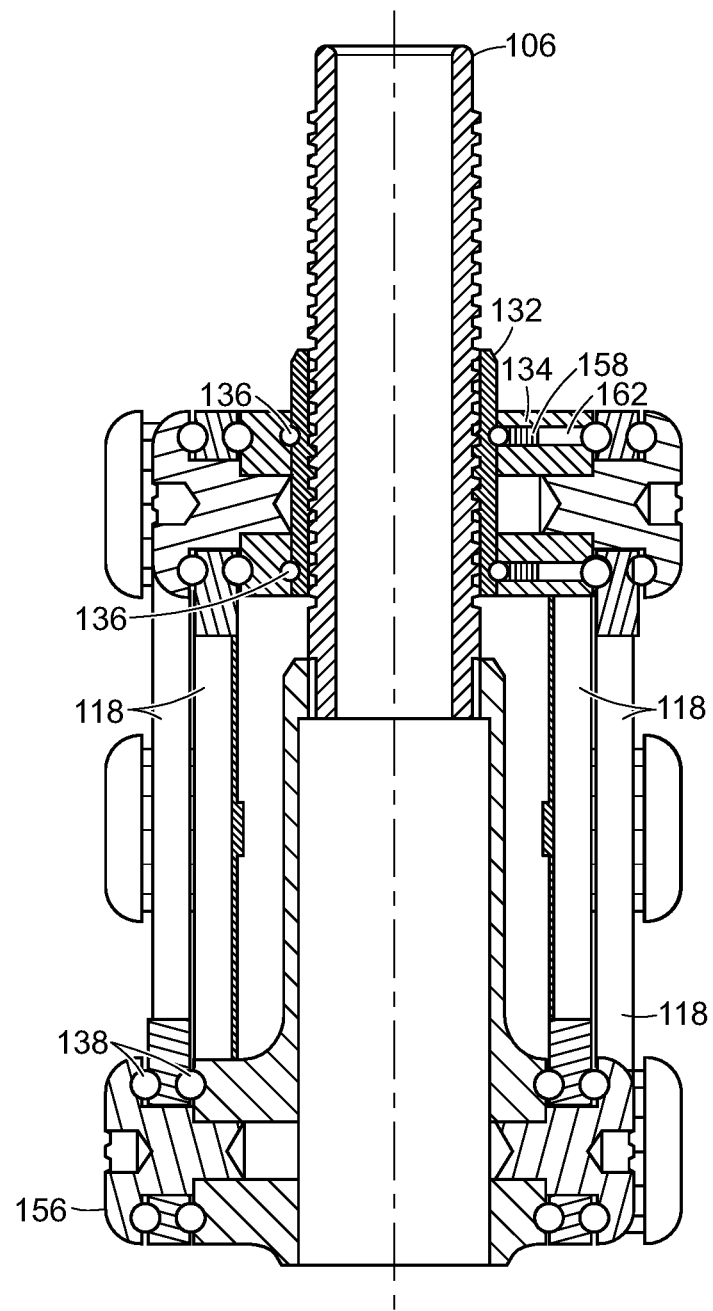
FIG. 6E is a cross-sectional view of a nut assembly coupled to a threaded pole of the vertebral body manipulation device according to an exemplary embodiment of the present disclosure.

A perspective view of the vertebral body manipulation device 100 is shown in FIG. 6A, and cross-sectional axes A-A and B-B, which are shown in FIGS. 6C and 6E, respectively, are noted.

As shown in FIG. 6A, scissor X mechanism 174 of module 110 may include two pairs of bars 118 that are interconnected with one another via central joint 124, thereby forming two X's, one on either side of the module 110 relative to axis A-A. The two X's are connected to module 110 via four revolute joints 122. Two of the four revolute joints 122 may be mounted to a base unit 120, one of the revolute joints 122 may be mounted to threaded coupling 133, and one of the revolute joints 122 may be mounted to slidable coupling 121. Threaded coupling 133 may be configured to mate with threaded pole 106, while slidable coupling 121 may be configured to mate with smooth pole 108 via bushing 128. Threaded pole 106 includes a nut assembly 140, described in FIG. 6B below, which includes a nut cage 134 configured to interface with nut 132.

In further embodiments, the threaded pole 106 and smooth pole 108 are hollow (e.g., pipe shaped) such that long instruments can be passed from the top to the bottom of the poles to access the heads of the pedicle screws 102 (not shown in FIG. 6A). Moreover, the bars 118 of the revolute joints 122 of the scissor mechanism 174 are mounted onto either fixed couplings (e.g., the lower revolute joints 122 mounted to base units 120) or the threaded coupling 133 or the slidable coupling 121 on threaded pole 106 and/or smooth pole 108. In the design described herein, any length of bar 118 is contemplated, and one of skill in the art will appreciate that this will vary depending upon the particular application. In general, the connection heights of revolute joints according to the invention will be minimized so that the joints are centered on the threaded pole 106 and smooth pole 108. Alternatively, these 4 revolute joints 122 may also be designed on opposite sides of the threaded pole 106 and smooth pole 108 (e.g., relative to axis A-A), if the threaded pole 106 and smooth pole 108 need to be brought into closer proximity. Placing the scissor X mechanism 174 on both sides is redundant, but may create a structure with improved stiffness.

Base units 120 may include button 112, which is configured to active a double cam closure mechanism that includes latch 126, and is further detailed below in FIG. 6C.

As shown in FIG. 6B, threaded pole 106 is threaded along its length and about the outside surface. In further embodiments, such a threaded pole 106 is a tubular shaped member. The threaded pole 106 comprises grooves 142 and a thread surface 144. The threaded coupling 133 may be threaded onto the threaded rod pole 106. In yet further embodiments, the thread surface 144 lends a mechanical advantage that allows the relative movement of the vertebral bodies 116 (see e.g., FIGS. 4 and 5).

As depicted in FIG. 6B, threaded coupling 133 includes nut assembly 140, which further includes a nut 132, a nut cage 134 configured to interface with grooves 142 of threaded pole 106, bearing balls 136 positioned between threaded coupling 133 and nut cage 134, thread surface 144 on an interior surface of nut cage 134, bushing surface 138, and a center of the nut 146. A rotary joint 182 is implemented between the nut 132 and the nut-cage 134 with two rows of bearing balls 136. While two bearing balls 136 are depicted, one of skill in the art will appreciated the number of bearing balls 136 within rotary joint 182 may be varied as desired.

Screw head locking can be achieved, for example, by locking nut 132 of the screw, or by using the quick-lock mechanism 150 (not shown) of the vertebral body manipulation device 100.

Due to the vertebral body manipulation device 100 kinematics as shown in FIG. 3, load in the SI direction generates lateral load between the pedicle screw 102 and the nut 132. Typical screw connections are not well suited for lateral loads, because of the wedging effect of the screw flanks. Instead, a modified ACME type thread with the bushing-nut (B-Nut) design shown in FIG. 6B was used. The ends of the nut 132 present cylindrical surfaces that are in a bushing surface 138 with the outer surface (major diameter) of the threaded pole 120. The actual thread of the nut 132 is only located at the center of the nut 146 where a larger clearance exists. To do so, the thread of the nut 132 has to be recessed deeper than the bushings surfaces 138, and therefore thread start grooves 142 are needed at the ends of the nut thread. The bushing surfaces 138 at the ends of the nut maintain clearance on the flanks of the thread surfaces 144.

As such, the screw is sized as an ACME thread screw of major diameter D. The bushings surfaces 138 (not shown) of the nut 132 are sized to with a H7/h6 tolerance from D. The thread 144 on the nut 132 is sized so that clearance between the flank surfaces of thread exists even if the bushing 128 is loaded laterally. That is:

$$C_{Min}^{T} = C_{Max}^{B} \sin \alpha \qquad \text{(Equation 1)}$$

where $C_{Min}^{T}$ is the minimum clearance on the thread flank, $C_{Max}^{B}$ is the maximum clearance of the bushing 128, and α is the angle of the thread flank (29° for the ACME thread). The design enables the lateral loads on the thread by eliminating the high friction wedging effect with a built-in bushing on the screw outer diameter. The gain is in lieu of a minimum axial backlash of the nut 132 relative to the screw.

$$B_{Min} = C_{Max}^{B} \sin 2\alpha \qquad \text{(Equation 2)}$$

The backlash is typically larger than that of a regular screw, where flank clearance may be used to control the backlash.

According to another aspect of the present disclosure there is featured an implant system embodying such a vertebral body manipulation device 100 described herein and a spinal implant as is known to those skilled in the art. In further embodiments, the spinal implant is operably coupled to the vertebral body manipulation device.

FIG. 6C shows a cross-sectional view of a module 110 of the vertebral body manipulation device according to an exemplary embodiment of the present disclosure along the A-A axis as noted in FIG. 6A. Threaded pole 106 may be configured to couple with threaded coupling 133 via nut 132 and nut cage 134, which interface on one surface directly with grooves 142 of threaded pole 106 while the opposite surface interfaces with the interior surface of threaded coupling 133 via rotary joint 186.

The smooth pole 108 may be configured to couple with slidable coupling 121 via bushing 128. Bars 118 and central joint 124 are shown for reference.

Quick-lock mechanism 150 may be configured to seat on or mate with screw extensions 104 to attach vertebral body manipulation device 100 with one or more vertebral anchors (not shown). Each screw extension 104 is fitted within receiving hole 154 of either threaded pole 106 or smooth pole 108. A latch 126 secures the screw extension 104 in position within the receiving hole 154 by inserting into geometric feature 125 when in the actuated position, thereby locking screw extension 104 into place. The latch 126 is actuated by a double-cam mechanism, including surfaces of the latch 126, the button 112, spring 148, and button-end part 152.

FIG. 6D is a cross-sectional view of a quick-lock mechanism of the vertebral body manipulation device in a closed (left panel) and opened (right panel) position according to an exemplary embodiment of the present disclosure. As depicted in FIG. 6D, when the button 112 is pressed (right panel), the top cam (button 112 to latch 126) pulls the latch 126 away from the geometric feature 125, which allows screw extension 104 to be inserted into and/or removed from receiving hole 154. When button 112 is pressed, the cam is in the unactuated (e.g., open) configuration.

When the button 112 is released (left panel of FIG. 6D), the spring 148 pushes up the button-end part 152, so that the bottom cam (button-end to latch, 152 to 126) pushes the latch 126 back into geometric feature 125, which locks screw extension 104 into place. After pushing the latch 126, the button-end part 152 also locks the latch 126 in the closed positon, as shown in the FIG. 6D, this ensuring a positive lock of the extension. When button 112 is released, the cam is in the actuated (e.g., closed) configuration.

FIG. 6E is a cross-sectional view along axis B-B of FIG. 6A of a nut assembly coupled to a threaded pole 106 of the vertebral body manipulation device 100 according to an exemplary embodiment of the present disclosure. Also visible in FIG. 6E is the design of the bearing balls 136. For each bearing ball 136, a channel 162 is made within the nut-cage 134 to allow the bearing balls 136 to be fed within their races, between the nut 132 and the nut-cage 134, that form the races of the bearing. While two bearing balls 136 are visible in FIG. 6E, one of skill in the art will appreciate that any number of bearing balls 136 appropriate for the size and configuration of the race may be used. The channels 162 are then closed with plugs 158. In embodiments, design consideration may be given to reduce the internal friction of the mechanism under load by, for example, adding additional bearings. Revolute joints 122 may be built with joint bearings 138 to reduce friction. A joint may be made, for example, by two rows of bearing balls 138 that sandwich one of the bars 118 with a bearing-race screw 156.

In further embodiments, the design of the vertebral body manipulation device 100 is optimized to reduce the change of its mechanical advantage due to the change in the relative angulation of the scissor X mechanism 174. FIG. 3 shows the location of the 4 side revolute joints 122 on the side of the threaded pole 106 and smooth pole 108, for the clarity of the schematic. However, in the design the length of the respective links is zero or negative (on the opposite side of the threaded pole 106 and smooth pole 108). The location of the revolute joints 122 relative to the threaded pole 106 and smooth pole 108 may be optimized to reduce sharp angles of the scissor X mechanism bars 174.

Pedicle Screw Lock

Pedicle screws 102 include ways to secure them to the connecting rods and lock their ball joint (from poly-axial to mono-axial in spine surgery terms). As shown in the cross section views of FIGS. 6C and 6E, both threaded pole 106 and smooth pole 108 of the vertebral body manipulation device 100 are hollow. Their inner diameter is large enough to allow the passage of the nut 132 of the pedicle screw 102 and its long wrench 114. If a rod is set in place over the screw head, the nut 132 can lock the head of the screw 102. This is typically performed after achieving the correction of deformity, so that the correction is secured by the screw-rod implant system.

As the vertebral body manipulation device 100 of the present disclosure embodies a quick lock mechanism 150 for coupling the instrument to any of a number of currently vertebral anchors, such as those embodying a utilizing polyaxial screw, such a vertebral body manipulation device is easily adaptable to use such a vertebral anchor.

According to further aspects, the present disclosure also feature methods for stabilizing a spine using such an implant system and/or reduction instrument/device as described herein. Also featured are methods for treating spondylolithesis using surgical techniques and using the vertebral body manipulation device and/or implant system of the present disclosure. Such methods are usable with both "open" surgical procedures and percutaneous pedicle screw techniques. Such methods further include continuous adjustment and manipulation of the vertebral segment to occur with intuitive uncoupled motion.

Figure 7:
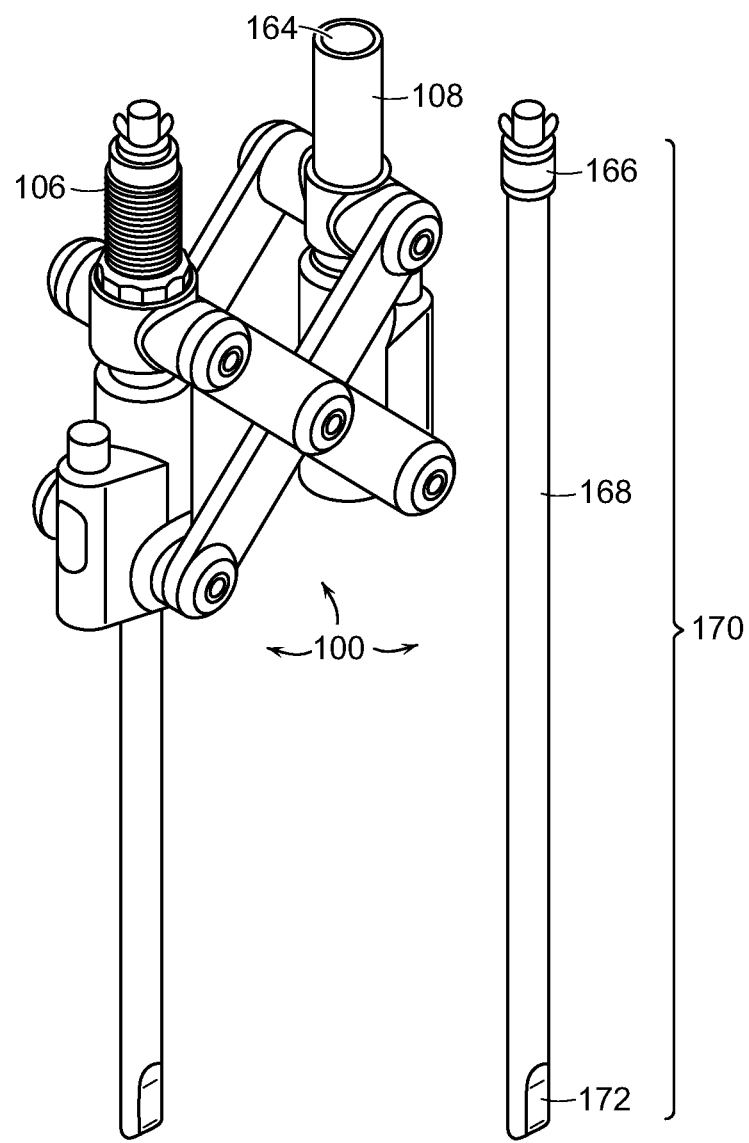
FIG. 7 is an illustrative view of the vertebral body manipulation device according to an exemplary embodiment of the present disclosure with pedicle screw locking plungers.

Such methods include providing one or more modules comprising any of the above described vertebral body manipulation device 100 and localizing the one or more modules 110 to a spinal implant and securing the vertebral body manipulation device to the spinal implant. The vertebral body manipulation device 100 includes an alternative screw-head locking mechanism that enables locking prior to placing the rods. Two lock plunger assemblies 170 are shown in FIG. 7, one placed in the primary device 130, the other separately.

In embodiments, the plunger assembly 170 consists of a threaded cap 166 that spins over a plunger 168. A plunger assembly 170 is placed through a threaded pole 106 or smooth pole 108 (e.g., via a smooth pole hole 164) and threaded cap 166 threads into the head of the screw extension 104. Tightening the thread pushes the plunger 168 down through the threaded pole 106 or smooth pole 108 and screw extension 104, so that the end surface of the plunger 172 locks the pedicle screw 102 by forcing it against its head.

In further embodiments, such methods further include performing other surgical techniques related to the surgical treatment of the underlying condition. Such other surgical techniques include fusion of adjacent vertebrae, bone grafting, discotomy, decompression or laminectomy and spinal implants. Additionally such methods for treating further includes, wound care and minimizing onset of infection.

Although a preferred embodiment of the disclosure has been described using specific terms, such description is for illustrative purposes only, and it is to be understood that changes and variations may be made without departing from the spirit or scope of the following claims.

INCORPORATION BY REFERENCE

All patents, published patent applications, and other references disclosed herein are hereby expressly incorporated by reference in their entireties.

EQUIVALENTS

Those skilled in the art will recognize, or be able to ascertain using no more than routine experimentation, many equivalents of the specific embodiments of the disclosure described herein. Such equivalents are intended to be encompassed by the following claims.

What is claimed is:

1. A vertebral manipulation instrument, comprising:
   at least one module including a first base unit, a second base unit, a threaded pole, a smooth pole, and a scissors mechanism;
   the first base unit having an upper end connected to the threaded pole and a lower end configured to mate with a first vertebral anchor;
   the second base unit having an upper end connected to the smooth pole and a lower end configured to mate with a second vertebral anchor; and
   the scissors mechanism connecting the first base unit to the second base unit and the threaded pole to the smooth pole,
   wherein the scissors mechanism connects to the threaded pole via a revolute joint.

2. The vertebral manipulation instrument of claim 1, wherein the scissors mechanism connects to the first base unit and the second base unit via a revolute joint.

3. The vertebral manipulation instrument of claim 1, wherein the scissors mechanism connects to the threaded pole via a revolute joint mounted on a threadable coupling configured to interface with a threaded portion of the threaded pole.

4. The vertebral manipulation instrument of claim 3, wherein the threadable coupling includes a rotary joint.

5. The vertebral manipulation instrument of claim 3, wherein the threadable coupling includes a nut and a nut cage configured to interface with a plurality of grooves on the threaded pole and a plurality of bearing balls positioned between the threaded coupling and the nut cage, the nut including a recessed thread configured to provide clearance relative to the plurality of grooves on the threaded pole.

6. The vertebral manipulation instrument of claim 1, wherein the scissors mechanism connects to the smooth pole via a revolute joint mounted on a slidable coupling configured to interface with a smooth portion of the smooth pole.

7. The vertebral manipulation instrument of claim 1, wherein the vertebral manipulation instrument is able to convey three degrees of freedom of movement to the first and second vertebral anchors when the lower end of the first base unit is mated with the first vertebral anchor and the lower end of the second base unit is mated with the second vertebral anchor.

8. The vertebral manipulation instrument of claim 1, wherein the first base unit and the second base unit each have a quick-lock mechanism configured to secure the first and second vertebral anchors.

9. A method for surgical treatment of spondylolithesis comprising the step(s) of: providing the vertebral manipulation instrument of claim 1, wherein each of the at least one modules is configured and arranged to cause translation or rotation of a vertebral segment along an Anterior-Posterior (AP), Superior-Inferior (SI), and/or Left-Right (LR) axis of a Left-Posterior-Superior (LPS) patient coordinate system.

10. The surgical treatment method of claim 9, further comprising the step(s) of: securing the manipulation instrument to a spine using spinal pedicle screw instrumentation.

11. A surgical manipulation instrument, comprising:
    at least one module including a first base unit, a second base unit, a threaded pole, a smooth pole, and a scissors mechanism;
    the first base unit having an upper end connected to the threaded pole and a lower end configured to mate with a first vertebral anchor;
    the second base unit having an upper end connected to the smooth pole and a lower end configured to mate with a second vertebral anchor; and
    the scissors mechanism connecting the first base unit to the second base unit and the threaded pole to the smooth pole, wherein the scissors mechanism confers three degrees of freedom of movement to the first and second vertebral anchors when the lower end of the first base unit is mated with the first vertebral anchor and the lower end of the second base unit is mated with the second vertebral anchor,
    wherein the scissors mechanism connects to the threaded pole via a revolute joint.

12. The surgical manipulation instrument of claim 11, wherein the threadable coupling is operated with a wrench.

13. The surgical manipulation instrument of claim 12, wherein the wrench is a torque wrench.

14. The surgical manipulation instrument of claim 11, wherein the scissor mechanism is configured to reduce changes in mechanical advantage.

15. The surgical manipulation instrument of claim 11, wherein the instrument is configured to maintain a head of the first vertebral anchor at the same relative orientation and level of a head of the second vertebral anchor.

16. The surgical manipulation instrument of claim 15, wherein the instrument is configured to adjust the distance between the head of the first vertebral anchor and the head of the second vertebral anchor.

17. The surgical manipulation instrument of claim 11, wherein the instrument is configured to manipulate one or more vertebral bodies by applying a rocking and/or twisting motion to the first and/or second vertebral anchors which have been anchored in the one or more vertebral bodies.

18. A vertebral body manipulation instrument (VBMI), comprising:
    a first support member having a first end and a second end, wherein a distal portion of the first end is threaded and the second end includes a fixed mounting portion and is configured to attach to a first vertebral anchor;
    a second support member having a first end and a second end wherein a distal portion of the first end is smooth and the second end includes a fixed mounting portion and is configured to attach to a second vertebral anchor;
    a threaded coupling configured to mate with the threaded first end of the first support member;
    a slidable coupling configured to slidably engage with the smooth first end of the second support member;
    a first crossbar;
    a second crossbar; and at least five revolute joints, wherein one revolute joint connects a middle portion of the first crossbar to a middle portion of the second crossbar to form a X-shaped structure in which the first crossbar spans between the threaded coupling and the fixed mounting portion of the second support member and the second crossbar spans between the slidable coupling and the fixed mounting portion of the first support member, and the VBMI is configured to maintain a head of the first vertebral anchor at the same relative orientation and level of a head of the second vertebral anchor.

19. The VBMI of claim 18, the instrument is configured to adjust the distance between the head of the first vertebral anchor and the head of the second vertebral anchor.

20. The VBMI of claim 18, wherein the instrument s configured to manipulate or more vertebral bodies by applying a rocking and/or twisting motion to the first and/or second vertebral anchors which have been anchored in the one or more vertebral bodies.

* * * * *